United States Patent [19]

Udaka et al.

[11] Patent Number: 5,411,886
[45] Date of Patent: May 2, 1995

[54] **XYLOSE ISOMERASE GENE OF *THERMUS AQUATICUS***

[75] Inventors: Shigezo Udaka, 1-24-3, Vezono-cho, Meito-ku, Nagoya-shi; Kenji Sakaguchi, Tokyo; Hideo Yamagata; Koen Dekker, both of Nagoya, all of Japan

[73] Assignees: Nihon Shokuhin Kako Co., Ltd., Tokyo; Shiogezo Udaka, Aichi, both of Japan

[21] Appl. No.: 112,630

[22] Filed: Aug. 27, 1993

Related U.S. Application Data

[63] Continuation of Ser. No. 783,150, Oct. 28, 1991, abandoned.

[30] Foreign Application Priority Data

Oct. 29, 1990 [JP] Japan .................. 2/291067
Mar. 7, 1991 [JP] Japan .................. 3/067967
Jun. 24, 1991 [JP] Japan .................. 3/178698

[51] Int. Cl.$^6$ .............. C12N 1/19; C12N 1/21; C12N 15/61; C12N 15/63
[52] U.S. Cl. .............. 435/252.3; 435/233; 435/234; 435/252.31; 435/252.33; 435/252.35; 435/254.21; 435/320.1; 536/23.2; 536/23.7
[58] Field of Search .............. 536/23.2, 23.7; 435/320.1, 252.3, 233, 234, 94, 252.31, 252.33, 252.35, 254.21

[56] References Cited

U.S. PATENT DOCUMENTS

| | | | |
|---|---|---|---|
| 4,352,881 | 10/1982 | Inagawa et al. | 435/17 |
| 4,593,001 | 3/1986 | Horwarth | 435/94 |
| 4,889,818 | 12/1989 | Gelfand et al. | 435/194 |
| 5,041,378 | 8/1991 | Drummond et al. | 435/69.1 |
| 5,310,665 | 5/1994 | Lambeir et al. | 435/234 |
| 5,340,738 | 8/1994 | Lambeir et al. | 536/23.2 |

FOREIGN PATENT DOCUMENTS

| | | |
|---|---|---|
| 0351029 | 1/1990 | European Pat. Off. |
| 0352474 | 1/1990 | European Pat. Off. |
| 89/01520 | 2/1989 | WIPO |

OTHER PUBLICATIONS

Lehmacher et al., "Isolation and characterization of an extremely thermostable D-xylose isomerase from *Thermus aquaticus* HB 8", 1990, *J. Gen. Microb.* 136: 679–686.

Scallet et al, "Studies in the Isomerization of D-Glucose", *Starch*, Dec. 1974, vol. 26, No. 12, pp. 405–408.

Lee et al, "Cloning and Expression of the *Clostridium thermosulfurogenes* Glucose Isomerase Gene in *Escherichia coli* and *Bacillus subtilis*", *Applied and Environmental Microbiology*, vol. 56, No. 9, Sep. 1990, pp. 2638–2643.

Dekker et al, "Xylose (Glucose) Isomerase Gene from the Thermophile *Thermus thermophilus*: Cloning, Sequencing, and Comparison with Other Thermostable Xylose Isomerases", *Journal of Bacteriology*, May 1991, vol. 173, No. 10, pp. 3078–3083.

Lehmacher et al., Biol. Chem. Hoppe-Seyler 371:527–536, Jun. 1990.

Stevis et al., *Enzyme Microb. Technol.* 7:592–596, Dec. 1985.

Adachi et al., *J. Bacteriology* 171:1010–1016, Feb. 1989.

Seno et al., *Mol. Gen. Genet.* 193:119–125, 1984.

*Primary Examiner*—Stephen G. Walsh
*Attorney, Agent, or Firm*—Burns, Doane, Swecker and Mathis

[57] ABSTRACT

A xylose isomerase gene from *Thermus* bacteria, such as *Thermos aquaticus* (ATCC 27634) and a gene having 60% or more of homology to the nucleotide sequence of *Thermus aquaticus* xylose isomerase gene of FIG. 1-3. A xylose isomerase from *Thermus aquaticus* characterized in that the xylose isomerase has the optimal pH of about 7, the stable pH range of from about 6 to 8.5, the optimal temperature of about 95° C. and the molecular weight of about 44,000, and is stabilized with manganese or magnesium. A process for preparing a xylose isomerase comprising transforming a microorganism with a plasmid containing the above gene and a promoter, culturing the transformed microorganism and harvesting the produced xylose isomerase. A process for preparing fructose comprising isomerization of glucose to fructose in the presence of the above xylose isomerase.

5 Claims, 10 Drawing Sheets

Figure 1

```
         10        20        30        40        50        60
GAGCTCCTCAAGGAGATGTCCGAAAGACTCGCTCATCTCTGCGCCATCGCCCTGAGCACC 70        80        90       100       110       120
TTGGACCCTGGGCTGGTGGTCCTCGGCGGCCCCCTCCGCCGAGGCTGCCGGGGAGAAGCT 130       140       150       160       170       180
TCTAGAGGAGGTGCGGAAGCCGGGCCTTTCCCCGCTACGCCCTGAAGGTGCATGAGCCCG 190       200       210       220       230       240
ACCAGGTGGTCCTTTCCCCCTTTGGACGGGATGCGGCCCTTCTGGGGGCAGGCGCCTTGG 250       260       270       280       290       300
CCGCAAGCCGATTTGTGGATTCCCTGGCTTTTGAGGAGGTGATGTAGGTGTACGAGCCCA
                                                   V  Y  E  P  K 310       320       330       340       350       360
AACCGGAGCACAGGTTTACCTTTGGCCTTTGGACTGTGGGCAATGTGGGCCGTGATCCCT
 P  E  H  R  F  T  F  G  L  W  T  V  G  N  V  G  R  D  P  F 370       380       390       400       410       420
TCGGGGACGCGGTTCGGGAGAGGCTGGACCCGGTTTACGTGGTTCATAAGCTGGCGGAGC
  G  D  A  V  R  E  R  L  D  P  V  Y  V  V  H  K  L  A  E  L 430       440       450       460       470       480
TTGGGGCCTACGGGGTAAACCTTCACGACGAGGACCTGATCCCGCGGGGCACGCCTCCTC
   G  A  Y  G  V  N  L  H  D  E  D  L  I  P  R  G  T  P  P  Q 490       500       510       520       530       540
AGGAGCGGGACCAGATCGTGAGGCGCTTCAAGAAGGCTCTCGATGAAACCGGCCTCAAGG
   E  R  D  Q  I  V  R  R  F  K  K  A  L  D  E  T  G  L  K  V 550       560       570       580       590       600
TCCCCATGGTCACCGCCAACCTCTTCTCCGACCCTGCTTTCAAGGACGGGGCCTTCACGA
   P  M  V  T  A  N  L  F  S  D  P  A  F  K  D  G  A  F  T  S
```

Figure 2

```
       610       620       630       640       650       660
GCCCGGACCCTTGGGTTCGGGCCTATGCCTTGCGGAAGAGCCTGGAGACCATGGACCTGG
  P  D  P  W  V  R  A  Y  A  L  R  K  S  L  E  T  M  D  L  G 670       680       690       700       710       720
GGGCAGAGCTTGGGGCCGAGATCTACGTGGTCTGGCCGGGCCGGGAGGGAGCTGAGGTGG
  A  E  L  G  A  E  I  Y  V  V  W  P  G  R  E  G  A  E  V  E 730       740       750       760       770       780
AGGCCACGGGCAAGGCCCGGAAGGTCTGGGACTGGGTGCGGGAGGCGCTGAACTTCATGG
  A  T  G  K  A  R  K  V  W  D  W  V  R  E  A  L  N  F  M  A 790       800       810       820       830       840
CCGCCTACGCCGAGGACCAGGGATACGGGTACCGGTTTGCCCTCGAGCCCAAGCCTAACG
  A  Y  A  E  D  Q  G  Y  G  Y  R  F  A  L  E  P  K  P  N  E 850       860       870       880       890       900
AGCCCCGGGGGGACATTTACTTCGCCACCGTGGGGAGCATGCTCGCCTTTATTCATACCC
  P  R  G  D  I  Y  F  A  T  V  G  S  M  L  A  F  I  H  T  L 910       920       930       940       950       960
TGGACCGGCCCGAGCGCTTCGGCCTGAACCCCGAGTTCGCCCACGAGACCATGGCCGGGC
  D  R  P  E  R  F  G  L  N  P  E  F  A  H  E  T  M  A  G  L 970       980       990      1000      1010      1020
TTAACTTTGTCCACGCCGTGGCCCAGGCTCTCGACGCCGGGAAGCTTTTCCACATTGACC
  N  F  V  H  A  V  A  Q  A  L  D  A  G  K  L  F  H  I  D  L 1030      1040      1050      1060      1070      1080
TCAACGACCAACGGATGAGCCGGTTTGACCAGGACCTCCGCTTCGGCTCGGAGAACCTCA
  N  D  Q  R  M  S  R  F  D  Q  D  L  R  F  G  S  E  N  L  K 1090      1100      1110      1120      1130      1140
AGGCGGCCTTTTTCCTGGTGGACCTCCTGGAAAGCTCCGGCTACCAGGGCCCCCGCCACT
  A  A  F  F  L  V  D  L  L  E  S  S  G  Y  Q  G  P  R  H  F 1150      1160      1170      1180      1190      1200
TTGACGCCCACGCCCTGCGTACCGAGGACGAAGAAGGGGTTTGGGCCTTCGCCCGAGGCT
  D  A  H  A  L  R  T  E  D  E  E  G  V  W  A  F  A  R  G  C 1210      1220      1230      1240      1250      1260
GCATGCGTACCTACCTGATCTTAAAGGAAAGGGCTGAAGCCTTCCGCGAGGATCCCGAGG
  M  R  T  Y  L  I  L  K  E  R  A  E  A  F  R  E  D  P  E  V 1270      1280      1290      1300      1310      1320
TCAAGGAGCTTCTTGCCGCTTACTATCAAGAAGATCCTGCGGCCTTGGCCCTTTTGGGCC
  K  E  L  L  A  A  Y  Y  Q  E  D  P  A  A  L  A  L  L  G  P
```

Figure 3

```
      1330      1340      1350      1360      1370      1380
CCTACTCCCGCGAGAAGGCCGAAGCCCTCAAGCGGGCGGAGCTTCCCCTCGAGGCCAAGC
  Y  S  R  E  K  A  E  A  L  K  R  A  E  L  P  L  E  A  K  R 1390      1400      1410      1420      1430      1440
GGCGCCGGGGTTATGCCCTGGAACGCCTGGACCAGCTGGCGGTGGAGTACCTCCTGGGGG
  R  R  G  Y  A  L  E  R  L  D  Q  L  A  V  E  Y  L  L  G  V 1450      1460      1470      1480      1490      1500
TGCGGGGGTGAGGGCGGCCATCGGCTTGGACCTGGGAACGAGCGGGCTCAAGGCCCTGGT
  R  G  *

1510      1520      1530      1540      1550      1560
GCTGGACGAGGAGGGGTAGAAAGCGCGCTGAGGCCCGGGCCGGTTACCCCCTTCACACCC 1570      1580      1590      1600      1610      1620
CGAGGCCGGGCTGGACGGAGCAGGACCCCCAGGACTGGGCCCGGGCCCTGAAGGAGGTGT 1630      1640      1650      1660      1670      1680
TCCGGGCCCTGGCGCCGAAGCTTTCGGGCTTGGAGGTGGTGGGCCTGGGGCTTTCCGGGC 1690      1700      1710      1720      1730      1740
AGATGCACGGGGCGGTCTTCCTGGACCGGGAGGGCCGTTTCCTCCTTCCTGCGCCCTTT 1750      1760      1770      1780      1790      1800
GGAACGACCAGCGCACGGAGGAGGAAGTCCGGTGGATGGAAGAGGTCTTCCCTCGGCCCG

AGCTC
```

XYLOSE ISOMERASE GENE OF THERMUS AQUATICUS

This application is a continuation of application Ser. No. 07/783,150, filed Oct. 28, 1991 now abandoned.

BACKGROUND OF THE INVENTION

The present invention relates to xylose isomerase genes of *Thermus* bacteria, especially *Thermus aquaticus* (hereinafter abbreviated as *T. aquaticus*), xylose isomerase produced by genetic engineering using the genes, a process for preparation of a xylose isomerase and a process for preparation of highly concentrated fructose using the xylose isomerase.

Xylose isomerases are enzymes that catalyze the interconversion between D-xylose and D-xylulose, and can also convert glucose into fructose which is important in industry.

*T. aquaticus* is a thermophilic bacterium, deposited as Accession Number ATCC 27634. *T. aquaticus* is also referred to as *Thermus thermophilus*. It has been reported that *T. aquaticus* produces a xylose isomerase (see, *Journal of General Microbiology* (1990), 136, 679–686), which was proven by the inventors to be a different enzyme from the enzyme produced by the present method in molecular weight, N-terminal amino acid sequence and others. *T. aquaticus* is a thermophilic bacterium and its xylose isomerase has a higher optimal temperature and thermal stability than *Clostridium thermohydrosulfuricum* xylose isomerase which also has an excellent thermostability compared to other isomerases which are presently utilized industrially. The enzyme is different, and any process for preparation of xylose isomerase in a large scale which is useful on an industrial scale is not yet known in the art.

Thus, once the xylose isomerase gene of *T. aquaticus* is obtained, it is possible to produce the *T. aquaticus* xylose isomerase in large scale by genetic engineering techniques. However, the isolation, identification and cloning of the *T. aquaticus* xylose isomerase gene has not been accomplished. Therefor, there is a need to provide the xylose isomerase gene of *T. aquaticus*.

The temperature at which a high fructose corn syrup (HFCS) is produced is conventionally selected at 60° C. based on the thermostability of the currently used isomerase. The fructose concentration in the product is dependent on the chemical equilibrium and is 42–45% in the case of the immobilized enzyme procedure at 60° C. But, in practical use, if the fructose concentration could be increased up to 55%, it may be used as a food sweetener for soft drinks without a further increase in fructose concentration. Then, if the production temperature could be raised to 85° C., the chemical equilibrium is shifted in the direction of more fructose production and it is possible to increase the fructose concentration to 55%.

SUMMARY OF THE INVENTION

The first object of the present invention is to provide xylose isomerase genes of *Thermus* bacteria especially *T. aquaticus*.

The second object of the present invention is to provide a process for efficiently producing the thermophilic and thermostable xylose isomerase using the xylose isomerase gene of *Thermus* bacteria, especially *T. aquaticus*.

The third object of the present invention is to provide a process for producing highly concentrated fructose by isomerizing glucose at a relatively high temperature at which the chemical equilibrium is shifted in direction of fructose production.

Further, when highly concentrated fructose is produced by isomerizing glucose, in order to optimize the isomerase activity, the pH of the reaction mixture may usually be adjusted. However, at the range of more than 7, a problem, that is, the coloring and the production of other by-products such as psicose in the resulting fructose solution occurs.

Thus, the fourth object of the present invention is to provide a process for producing relatively colorless and highly concentrated fructose by isomerizing glucose at the specific pH range using the thermostable xylose isomerase obtained by the process as described above.

The present inventors established the method to isolate the xylose isomerase gene of *Thermus* bacteria such as *T. aquaticus*, to determine its base sequence and amino acid sequence, and to clone the gene. Then, the inventors found the method to produce the thermostable xylose isomerase efficiently by genetic engineering techniques using the cloned xylose isomerase gene.

Moreover, it was found that the xylose isomerase of *T. aquaticus* made by the genetic engineering method was unexpectedly different from the native xylose isomerase obtained from *T. aquaticus* and had excellent characteristics compared to the native one (see, *Journal of General Microbiology* (1990), 136, 679–686).

Additionally, it was found that fructose could be produced at a higher temperature by using the present xylose isomerase. Further, by performing the isomerization using the present xylose isomerase at a higher temperature than 75° C. and at a pH value ranging from 5 to 7, it was found that more concentrated fructose with extremely low coloring could be produced.

BRIEF DESCRIPTION OF THE DRAWINGS

FIGS. 1 to 3 show the base sequence [SEQ ID NO: 1 and 2], and the amino acid sequence of the xylose isomerase gene of *T. aquaticus* of the present invention.

Figure 4:
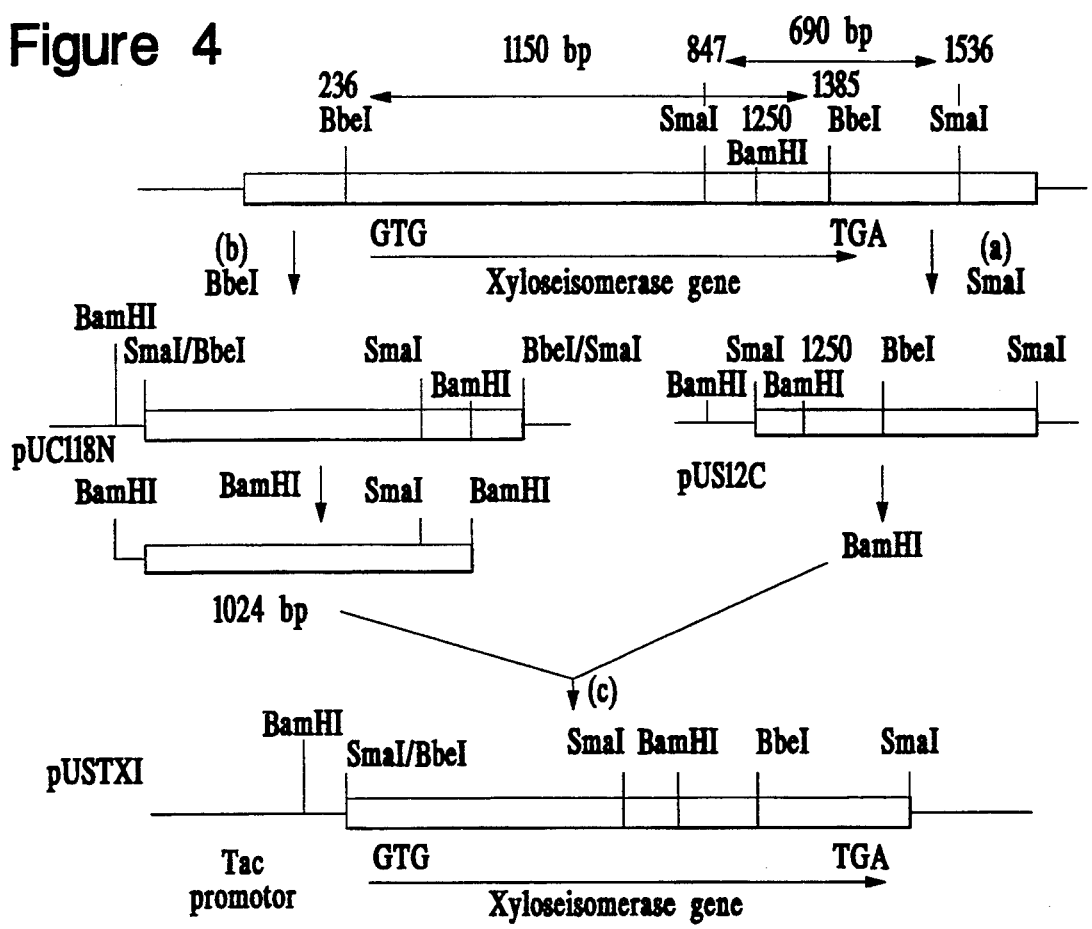
FIG. 4 is a scheme illustrating a constructing process of plasmid pUSTXI containing the xylose isomerase gene.

The present invention will be described in detail.

The present xylose isomerase gene of *T. aquaticus* has, for example, the base sequence and the amino acid sequence [SEQ ID NO: 1 and 2] shown in FIGS. 1–3. However, the base sequence and the amino acid sequence shown in FIGS. 1–3 are an example of xylose isomerase gene of *T. aquaticus* and therefore, xylose isomerases may be obtained with the genes which have a certain degree of homology to the gene set forth in FIGS. 1–3.

Accordingly, from this viewpoint, the xylose isomerase genes of the present invention include genes which have more than 60% homology to the amino acid sequence of the xylose isomerase gene shown in FIGS. 1-3. A higher homologous gene provides an enzyme closer to the natural xylose isomerase. Thus, the xylose isomerase genes of the present invention include genes encoding nucleotide sequences which have preferably more than 70%, more preferably more than 80% and most preferably more than 90% homology to the nucleotide sequence of the xylose isomerase gene shown in FIGS. 1-3.

Further, the xylose isomerase genes of the present invention include genes obtained from *Thermus* bacteria other than *T. aquaticus*. Examples of *Thermus* bacteria include *Thermus flavus* (ATCC 33923), *Thermus lacteus* (ATCC 31557), *Thermus rubens* (ATCC 31556), *Thermus sp.* (ATCC 27737, 27978, 31674).

For example, xylose isomerase genes of *T. aquaticus* can be prepared by cloning them into *E. coli* with the method described in Examples.

*T. aquaticus* xylose isomerase can be obtained by inserting the above xylose isomerase gene into a plasmid with a suitable promoter and transforming microorganisms with the resulting plasmid. Examples of these microorganisms include *E. coli, Bacillus brevis, Saccharomyces cerevisiae, Streptomyces lividans* and *Bacillus subtilis*. Promoters suitable to these microorganisms are used.

In *E. coli*, for example, tac promoter (*Agric. Biol. Chem.* 52(4), 983-988, 1988) and phage T7 promoter (F. W. Studier et al., *Methods in Enzymol.*, 185, 60-84, 1989) can be used. For instance, the xylose isomerase can be prepared by inserting the above-mentioned xylose isomerase gene into plasmid pUS12, transforming *E. coli* with this plasmid, culturing the transformant and harvesting the produced xylose isomerase. Plasmid pUS12, developed by Shibui et al., contains a strong and expression-controllable tac promoter (*Agric. Biol. Chem.*, 52(4), 983-988, 1988).

In *Bacillus brevis*, the xylose isomerase can be prepared by using cell wall protein (CWP) promoter (Adachi, T., Yamagata, H. et al., *J. Bacteriol.*, 171, 1010-1016, 1989) to transform *Bacillus brevis*, culturing the transformant at 30° C. in, for example, a beef extract, glucose and peptone medium (pH 7.0), and harvesting the produced xylose isomerase.

In *Saccharomyces cerevisiae*, the xylose isomerase can be prepared by using PGK (the promoter of phosphoglycerate kinase gene), ADC (the promoter of alcohol dehydrogenase) or GAP (the promotor of glyceral aldehyde phosphate dehydrogenase) (L. Guareente, M. Ptashne, *Proc. Natl. Acad. Sci. USA*, 78, 2199-2203, 1988) to transform *Saccharomyces cerevisiae*, culturing the transformant at 30° C. in, for example, the medium composed of 0.3% yeast extract, 2% sucrose, 0.5% peptone, 0.1% $KH_2PO_4$, 0.05% $MgSO_4 \cdot 7H_2O$ (pH 5.5), and harvesting the produced xylose isomerase.

In *Streptomyces lividans* 66, the xylose isomerase can be prepared by using gyl P1 (glycerolkinase P1 gene) promoter (E. T. Seno et al., *Mol. Gen. Genet.*, 193, 119-125, 1984), ermEP1 (erythromycin resistance gene EP1) promoter (C. J. Thompson et al., *J. Bacteriol.*, 51, 678-687, 1983) to transform *Streptomyces lividans* 66, culturing the transformant by the method of C. J. Thompson et al. and harvesting the produced xylose isomerase. In Thompson et al. the cultures were grown at 32° C. until early stationary phase. Mycelium was collected by centrifugation for 5 min at 4,000×g and then suspended and pelleted three times in cold (4° C.) RS buffer (10mM Tris-hydrochloride [pH 7.6] at 20° C., 10 mM $MgCl_2$, 50 mM $NH_4Cl$, 3 mM 2-mercaptoethanol). When required for rRNA methylation assays, extracts were prepared by grinding with alumina (28). Otherwise, mycelium was disrupted by sonication. About 1 ml of packed, washed mycelium (obtained from a 25-ml culture) was suspended in 4 ml of RS buffer and placed in an ice bath. Sonication was performed in three bursts of 10 s each followed by a 10-s cooling period, using a Dawe Soniprobe. Cell debris was then removed by centrifugation at 15,000 rpm for 30 min at 4° C. in a Sorvall SS34 rotor. The supernatant was used directly in radiochemical assays of antibiotic modification. When, however, extracts were to be used in spectrophotometric assays of phosphotransferase activity, NADH oxidases were removed by further centrifugation at 100,000×g for 90 min at 4° C. in an MSE Prepspin 10×10 rotor.

The xylose isomerases obtained by the above-mentioned genetic engineering techniques are unexpectedly different from the known native xylose isomerase (*Journal of General Microbiology* (1990), 136, 679-686) and are found to be novel xylose isomerases.

The present xylose isomerases characteristically have the optimal pH of about 7, the stable pH range of from about 6 to 8.5, the optimal temperature of about 95° C. and the molecular weight of about 44,000, and are thermally stabilized with manganese or magnesium and destabilized with cobalt.

On the other hand, the natural xylose isomerase has the wide optimal pH range of from 5.5 to 8.5 and the stable pH range of from 6 to 9. In respect to metals, the natural one is thermally stabilized with manganese or cobalt. However, unlike the present xylose isomerases, it is not stabilized with magnesium but is destabilized. The optimal temperature is about 85° C., being lower by about 10° C. than that of the present xylose isomerases. The molecular weight is 50,000 and is clearly larger than that of the present xylose isomerases. Moreover, its N-terminal amino acid sequence (H. Bisswanger, personal communication) is Ser-Tyr-Phe-Pro-Asp-Ile-Gly-Lys-Ileu-Ala-Tyr-Glu-Gly-Pro-Glu-Ser-Arg-Asn-Pro-Lys- which is totally different from the N-terminal sequence of this invention.

Although both the present xylose isomerases and the natural xylose isomerase are derived from *T. aquaticus*, they are different enzymes. The reasons are inferred as follows. The natural xylose isomerase is directly harvested from *T. aquaticus*. In contrast, the present xylose isomerases are obtained by use of a cloned gene *T. aquaticus*. Thus, it is possible that *T. aquaticus* has two or more kinds of xylose isomerase genes and in the present invention, a xylose isomerase gene different from that of the natural xylose isomerase may be obtained.

The novel xylose isomerase of the present invention catalyze the isomerization between fructose and glucose. The activity of the isomerase is determined by, for example, the following method: 0.1-0.4U xylose isomerase is incubated at 85° C. in 1 ml of an aqueous solution of 100 mM Hepes (pH 7), 400 mM fructose and 10 mM $MnCl_2$. The yield of glucose is determined by analyzing 20 µl of a sample by the glucose oxidase analysis method (glucose-B-test, Wako Junyaku in Japan). One unit is defined as the amount of enzyme forming 1 µ mole of glucose in one minute under the conditions described above.

As described in the Examples, purification of the present xylose isomerase is performed as follows: Transformants that have been transformed with the present xylose isomerase gene are cultured and the resulting cells are harvested by centrifugation. The precipitate is resuspended in 2 ml of 1000 mM triethanolamine buffer (pH 7) containing 10 mM $MnCl_2$ and 400 mM fructose, and lysed with sonification. The resulting debris are removed by centrifugation. The cell extract is heated for 10 minutes at 85° C. and then the denatured protein is removed by centrifugation. The supernatant is purified by ultrafiltration against 500 volumes of 50 mM Hepes (pH 7), 5 mM EDTA buffer and the same buffer without EDTA each two times.

The molecular weight of the present xylose isomerase is about 44,000, and the gene thereof encodes a polypeptide of 387 amino acids. The thermostability of this xylose isomerase is increased by addition of manganese or magnesium, compared to that without such metals. Further, by addition of cobalt, the xylose isomerase shows lower thermostability than that without cobalt. The present xylose isomerase has the optimal temperature of about 95° C.

In an aspect of the present invention, highly concentrated fructose is produced by isomerizing glucose at higher temperature, i.e., more than 75° C., preferably more than 80° C. in the presence of the xylose isomerase described above. Since, in the view of chemical equilibrium, a higher reaction temperature results in higher concentrated fructose, it is preferred that the reaction temperature is controlled at a temperature as high as possible. *T. aquaticus* xylose isomerase obtained by the genetic engineering method described above, has an optimal temperature for isomerase activity at about 95° C. Therefore, from the point of enzymatic activity, it is preferred that the reaction temperature is controlled at around 95° C. Practically, the reaction is suitably conducted at 100° C. or less, preferably 80°–95° C.

On the other hand, the pH value of the reaction mixture to be efficient is 5–7, preferably 5–6.5 from the viewpoint of avoiding coloring the resulting fructose solution.

Isomerization of glucose with the xylose isomerase may be performed by either batch method or continuous method with immobilized enzyme. In the batch method, the reaction time may be changed depending on the scale of reaction and may ranges, for example, from about 1 to 24 hours. In the continuous method using the immobilized enzyme, the retention time may, for example, be approximately 1 minute to 24 hours, preferably approximately 5 minutes to 3 hours.

EXAMPLE 1

Strain:
*Thermus aquaticus* HB8: ATCC 27634 *E. coli* JM109: recA1supE44endA1hsdR17gyrA96relA1thiΔ (lac-proAB)F'[traD36proAB+lac$^q$ lacZΔ M15 ]
Culture condition

*T. aquaticus* is grown by the method of Nagahari et al. (Nagahari et al., Gene, 10, 137–145, 1980). *E. coli* cells are grown at 37° C. in twofold concentrated yeast extract-tryptone broth (available from Difco in U.S.A.) described in the method of Vieira et al. (Vieira et al., Meth. Enz., 1987, 153 (3–11)).
Cloning and sequencing procedures Genome DNA was extracted from *T. aquaticus* cell by the method of Saito [Saito, H. and Miura, K., "Preparation of transforming DNA by phenol treatment," Biochim. Biophys. Acta 1963, 72(619–629)]. Freezed pellet (0.45 g) was resuspended in 4.5 ml of 200 mM NaCl, 100 mM EDTA, 50 mM Tris-HCl (pH 8.0). After addition of 0.5 ml of 10% SDS, the mixture was mildly rotated for 15 min at 60° C., and subsequently treated with RNase A (0.05 mg/mi) for 30 min at 60° C. Additionally, it was treated with proteinase K (0.5 mg/ml) for 60 min at 60° C. This lysate solution was added with the same volume of phenol solution (saturated with Tris buffer) to remove the denatured protein. These procedures were repeated three times. The residue was removed by centrifugation (10 min, 15000 rpm).

After addition of 0.8 volume of isopropanol, DNA was wound up and resuspended in 1.5 ml of 10 mM Tris-HCl (pH 8.0) containing 1 mM EDTA. Finally, the DNA was purified with anion exchange chromatography using a DEAE cellulose column (washing buffer: 50 mM Tris HCl, pH 8.0, 1 mM EDTA, 0.15 M NaCl; elution buffer: 50 mM Tris HCl, pH 8.0, 1 mM EDTA, 1M NaCl).

The genome DNA was digested with SacI. The fragments were fractionated with 0.4% agarose gel electrophoresis. The DNA was denatured by immersing the gel in 1.5M NaCl, 0.5M NaOH for 25 min. The gel was neutralized with 3M sodium acetate (pH 5.5). The DNA was transferred to a nylon membrane (available from Biodyne in Glen Cove, N.J., U.S.A.) by electroblotting (3h, $2mA/CM^2$) and treated at 80° C. for 1 hour. This blot was hybridized with $^{32}$P-labelled 287 nucleotides long BglI fragment from *Streptomyces griseofuscus* S-41 xylose isomerase gene ($10^6$ pm/ml) at 54° C. As shown by comparison with nucleotide sequences of xylose isomerases obtained from *Bacillus subtilis*, *E. coli*, *Streptomyces violaceoniger* and *Ampullariella*, this fragment contains two relatively high homologous regions. After hybridization, a single band appeared around 1.8 Kb range.

The 1.8 Kb±0.5 Kb fragment from *Thermus* DNA digested with SacI was isolated by extraction and glass milk and ligated into *E. coli* vector pIC18 digested with SacI. Competent *E. coli* JM109 cell was transformed with the ligated DNA. Colonies having the desired Thermus DNA were detected by hybridizing the transformant colonies with *S. griseofuscus* probes. Plasmid DNA was extracted from the colonies showing a positive signal by the alkaline lysis method, and analyzed by digestion with restriction enzymes and Southern hybridization.

A 1.8 Kb SacI fragment that was strongly hybridized with the probe obtained from *S. griseofuscus* xylose isomerase gene was obtained. This 1.8 Kb fragment was cleaved to smaller fragments with restriction enzymes. These fragments were subcloned into *E. coli* JM109 using pUC118 and pUC119. A single-stranded DNA was prepared according to the method of Vieira described above and sequenced with TaqDNA polymerase (AmpliTaq ® sequencing kit: available from Takara Shuzo Co., Ltd. in Japan) and 7-deaza dGTP.

The base sequence and the amino acid sequence of *T. aquaticus* xylose isomerase gene are shown in FIGS. 1–3. Alternatively, each homology of amino acid sequence between the present *T. aquaticus* xylose isomerase and the above xylose isomerases obtained from microorganisms other than *T. aquaticus* is shown in Table 1.

TABLE 1

| Microorganism | Homology (%) |
| --- | --- |
| *Streptomyces griseofuscus* | 59 |
| *Streptomyces violaceoniger* | 58 |
| Ampullariella sp | 54 |
| *Actinoplanes missouriensis* | 55 |
| *Clostridium thermohydrosulfuricum* | 27 |
| *Clostridium thermosulfuricum* | 29 |
| *Bacillus subtilis* | 27 |
| *Escherichia coli* | 26 |

EXAMPLE 2

The xylose isomerase gene of *T. aquaticus* was inserted in *E. coli* expression vector pUS12 [*Agric. Biol. Chem.*, 52(4), 983–988, 1988] as follows:

(a) First, the 690 bp SmaI fragment encoding the C-terminal region of xylose isomerase (in FIGS. 1–3, from the 847th base to the 1536th base) was inserted into the SmaI site of pUS12, resulting in pUS12C.

(b) The 1150 bp BbeI fragment encoding the N-terminal region of xylose isomerase (in FIGS. 1–3, from the 236th base to the 1385th base) was blunt-ended and inserted into the SmaI site of pUC118N. resulting in pUC118N.

(c) The 1024 bp BamHI fragment containing the region from the BamHI site upstream the insertion site of pUS12C to the BamHI cutting site of the inserted fragment (in FIGS. 1–3, the 1250th base) was substituted with the fragment between the BamHI site upstream the insertion site of pUS12C constructed in (a) and the BamHI cutting site in the inserted fragment (FIGS. 1–3, the 1250th base).

The resulting plasmid pUSTXI had an inserted whole xylose isomerase gene containing a translational start codon between the BamHI site and the SmaI site of pUS12.

Transformants that were obtained by transformation of *E. coli* JM109 with the resulting plasmid pUSTXI were grown up to the mid-log phase (A660 ca. 1.0) at 37° C. in 3 ml of twofold concentrated yeast extract-tryptone broth (available from Difco in U.S.A.) according to the method of Vieira et al. (Vieira et al., *Meth. Enz.* 1987, 153(311)). Then, the tac promoter was activated by addition of 1 mM isopropyl-thiogalactoside (IPTG) and subsequently transformants were grown for another 2.5 hours. Cells were harvested by centrifugation and resuspended in 2 ml of 100 mM triethanolamine buffer (pH 7) containing 10 mM $MnCl_2$ and 400 mM fructose, and lysed with ultrasonification. The resulting debris were removed by centrifugation. The cell extracts were heated at 85° C. for 10 min. and the denatured protein was removed by centrifugation.

The assays of xylose isomerase activity in 200 μl of heat-treated cell extract were performed by determining the amount of glucose formed at 85° C. in 1 ml of 100 mM triethanolamine buffer (pH 7) containing 10 mM $MnCl_2$ and 400 mM fructose (glucose-B-test available from Wako in Japan). Activity of xylose isomerase and its yield in culture medium are shown in Table 2.

For comparison, the activity of xylose isomerase in 200 μl of heat-treated cell extract obtained with *E. coli* harboring vector pUC119 which has no isomerase gene and the yield in culture medium are shown in Table 2.

TABLE 2

| Strain | Activity (μ mol/min mg) | Yield (U/liter culture) |
| --- | --- | --- |
| *E. coli*:pUSTXI | 3.9 | 450 |
| *E. coli*:pUC119 | 0.1 | 10 |

The supernatant of cell extract obtained by removing protein which was denatured by heating at 85° C. for 10 min. with a centrifuge and was purified with ultrafiltration against 500 volumes of 50 mm Hepes, pH7, 5 mm EDTA buffer and the same buffer without EDTA, each two times, thereby the present xylose isomerase was obtained.

EXAMPLE 3

On the present xylose isomerase, optimal pH, stabilizing pH range, thermostabilization with metals, optimal temperature and molecular weight were determined.

Optimal pH

Figure 5:
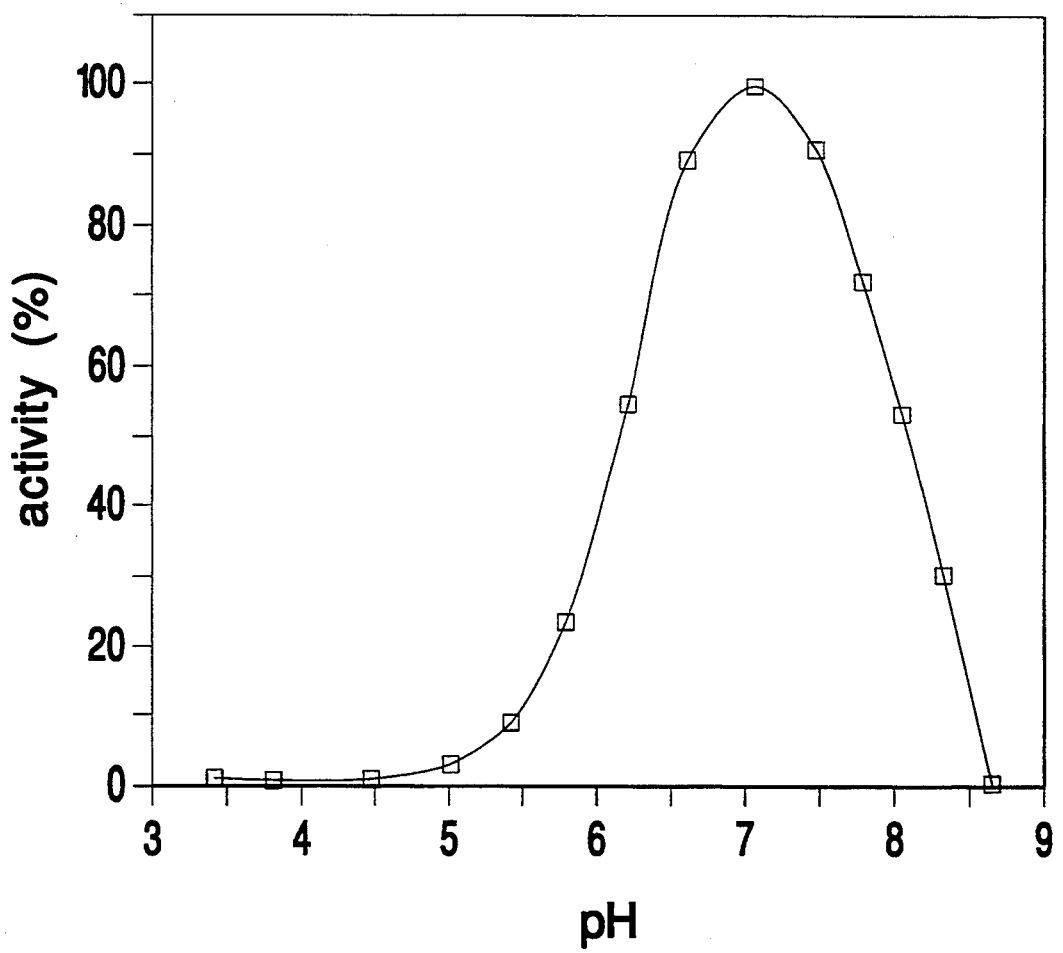
FIG. 5 illustrates a pH dependence of the activity of the present xylose isomerase.

The optimal pH of the present xylose isomerase in the case of 85° C. was determined by incubating it in a buffer containing 50 mM N-2-hydroxyethylpiperadine-N'-2-ethane sulfonic acid, 50 mm glycine, 400 mM fructose and 10 mM $MgCl_2$ at 85° C. for 0, 8 or 16 min. The pH value of each sample was determined by adjusting it with NAOH at 80°. The yields of glucose were determined with the glucose-B-test (available from Wako Junyaku in Japan). The results are shown in FIG. 5.

PH stability

Figure 6:
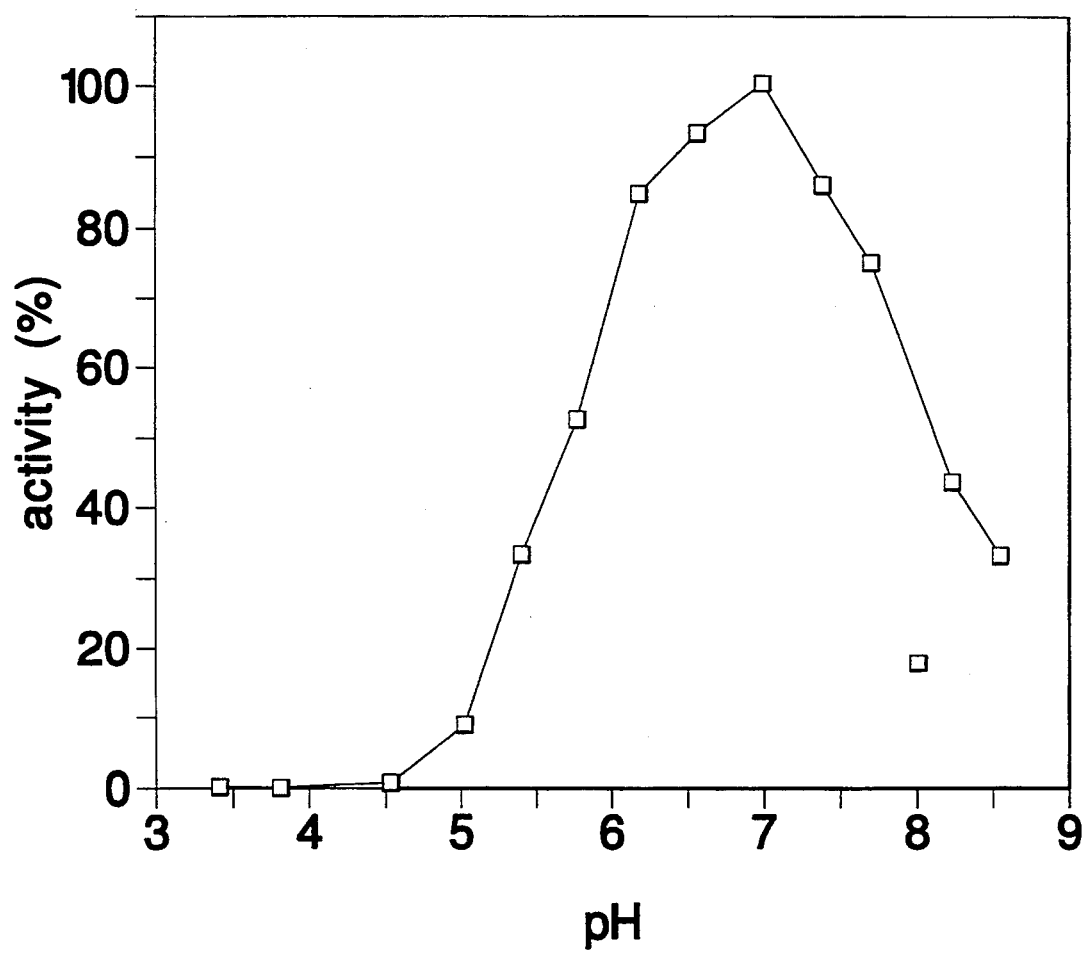
FIG. 6 illustrates a pH dependence of the stability of the present xylose isomerase.

The pH stability of the present xylose isomerase at 90° C. was determined by incubating it in a buffer containing 25 mM acetic acid, 25 mM piperidine-N,N'-bis(2-ethanesulfonic acid), 25 mM N-2-hydroxyethyl-piperadine-N'-2-ethanesulfonic acid, 25 mM glycine and 5 mM $MgCl_2$ at 90° C. The pH value of each sample was determined by adjusting it with NaOH at 80° C. After incubation, 40 μl sample was incubated with 760 μl reaction mixture containing 100 mM triethanolamine, pH7, 400 mM fructose and 10 mM $MgCl_2$ at 95° C. for 0, 8 and 16 min. and the residual activity was determined. Yield of glucose was determined with the glucose-B-test (available from Wako Junyaku in Japan). The results are shown in FIG. 6.

Stabilization with metals

Figure 7:
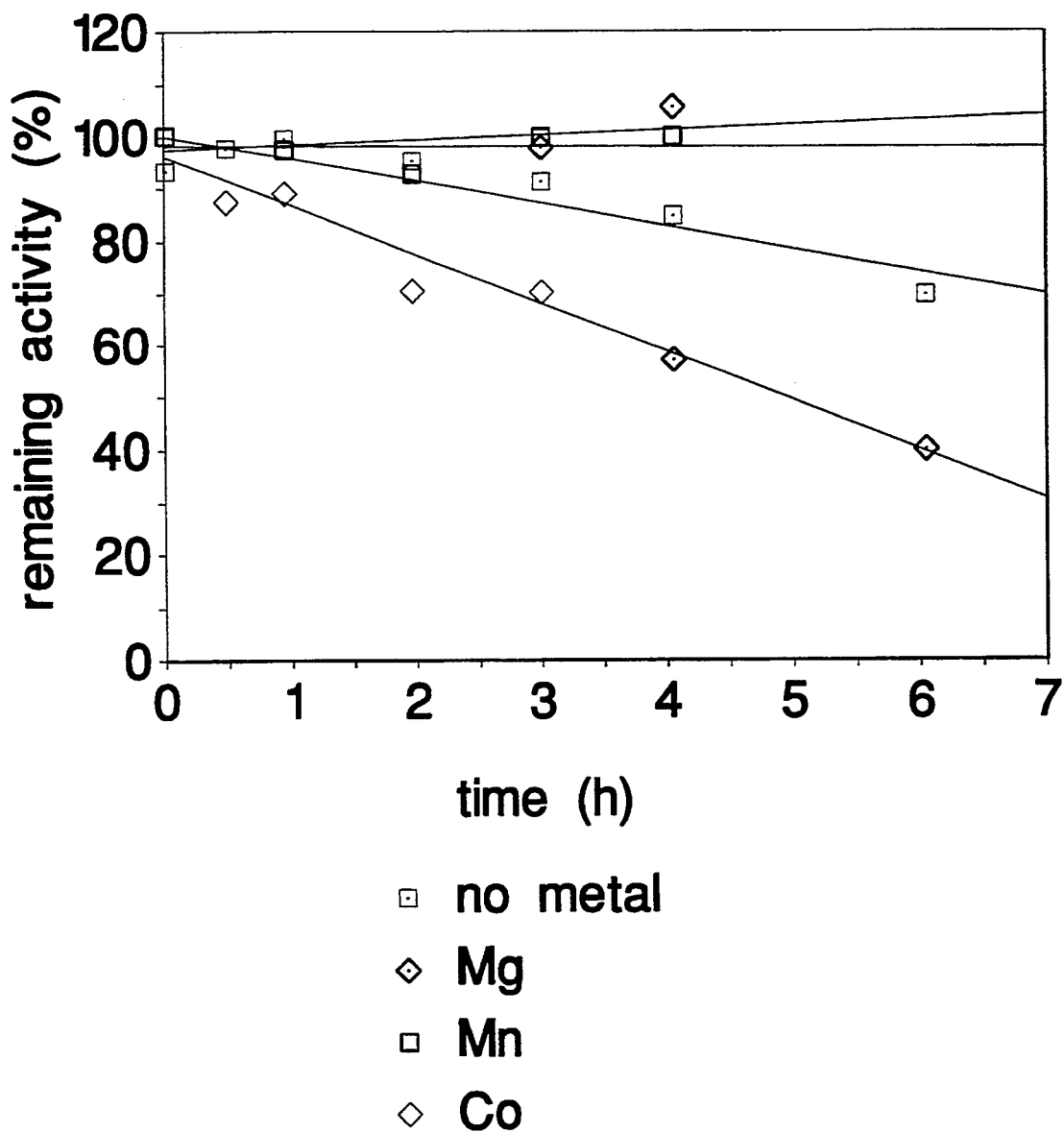
FIG. 7 illustrates effects of metals to the thermal stability of the present xylose isomerase.

In order to determine the effects of metals on the thermostability of the present xylose isomerase, it was incubated in a buffer containing 100 mM Hepes, pH7, 400 mM fructose and 5 mM each metal salt ($MnCl_2$, $MgCl_2$, $CoCl_2$) at 90° C. for 30 min., 1h, 2h, 3h, 4h or 6h. After incubation, 40 μl sample was incubated with 1 ml reaction mixture containing 100 mM triethanolamine, pH7, 400 mM fructose and 10 mM $MgCl_2$ at 85° C. for 8 or 16 min., and the residual activity was determined. Yield of glucose was determined with the glucose-B-test (available from Wako Junyaku in Japan) using glucose oxidase. The results are shown in FIG. 7.

Optimal temperature (temperature dependence of isomerase activity)

Figure 8:
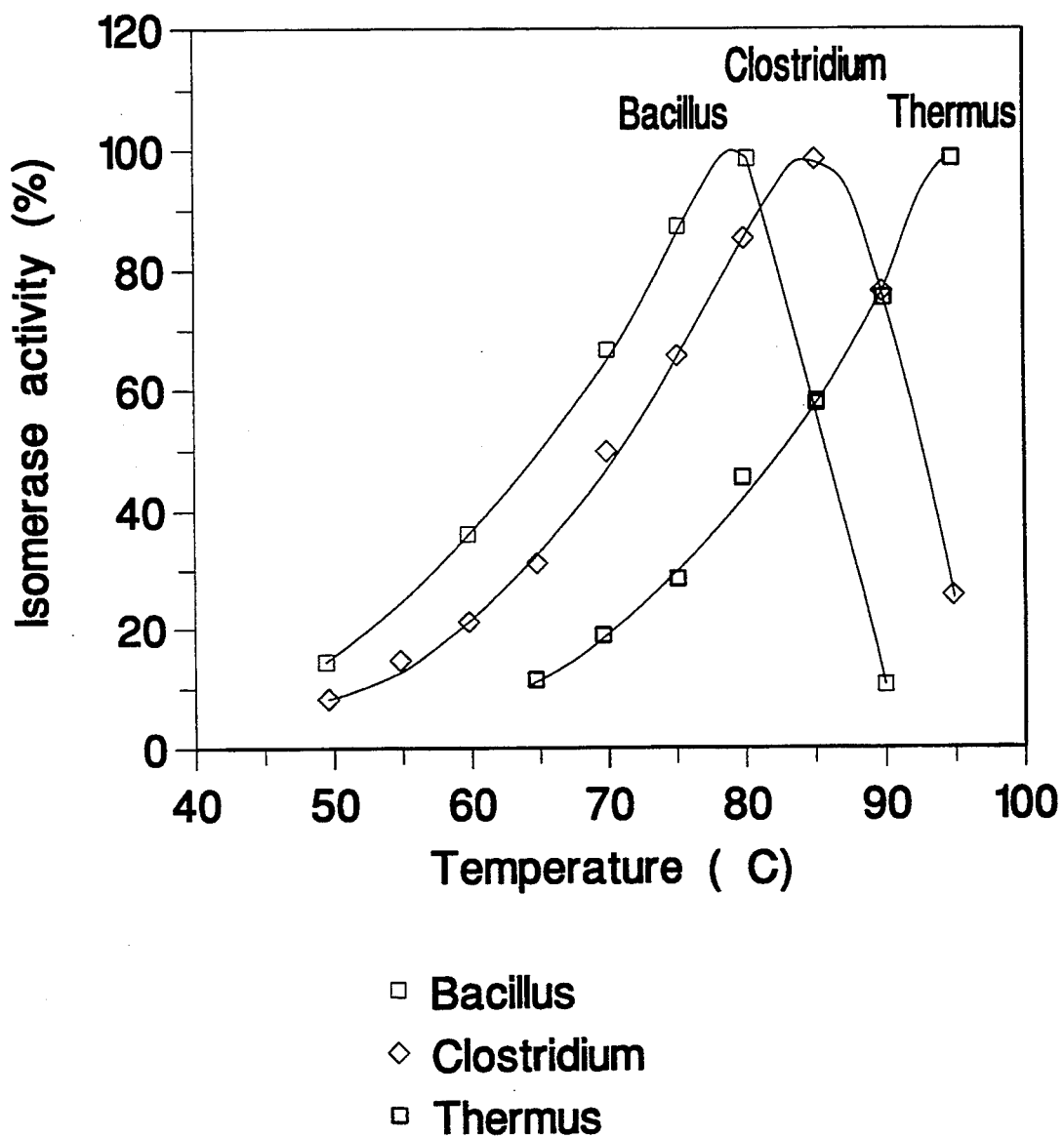
FIG. 8 illustrates a temperature dependence of the activity of xylose isomerases.

After incubation of the reaction mixture containing 400 mM fructose, 100 mM triethanolamine buffer (pH7), 50 mM $Mg^{2+}$ and $Co^{2+}$ with the present xylose isomerase at 65°, 70°, 75°, 80°, 85°, 90° or 95° C., conversion rate of fructose into glucose was determined with the glucose-B-test (available from Wako Junyaku in Japan). The results, as well as the results on the temperature dependence of isomerase activity of *Bacillus* and *Clostridium* xylose isomerase are shown in FIG. 8. The temperature dependence of isomerase activity of Bacillus or Clostridium xylose isomerase was determined using a mixture containing 400 mM fructose, 100 mM triethanolamine buffer (pH7), 50 mM $Mg^{2+}$ and xylose isomerase in the same manner as above.

Molecular weight

The molecular weight of the present xylose isomerase determined by SDS-PAGE was shown to be 44,200. It is approximately consistent with the theoretical molecular weight, 43,900, calculated with the amino acid sequence of the xylose isomerase gene.

EXAMPLE 4

Figure 9:
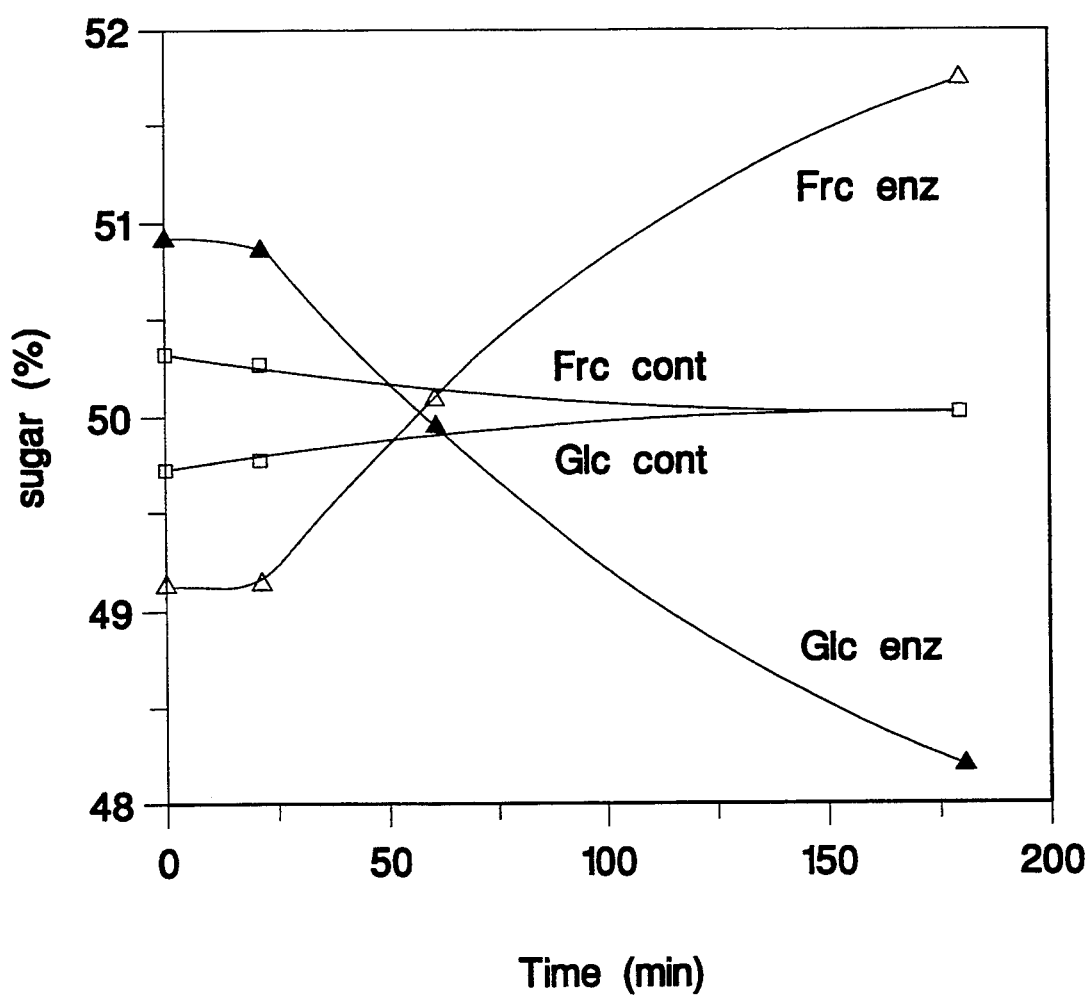
FIG. 9 illustrates results of isomerization reaction of glucose to fructose using the present xylose isomerase.

Isomerization of glucose to fructose was performed by using the xylose isomerase of the present invention. The reaction mixture containing 25%(W/V) fructose, 25%(W/V) glucose, 5 mM $MnCl_2$ and 100 mM MOPS (3-(N-morpholino) propanesulfonic acid) buffer (pH 6.5, at 25° C.) was prepared. This solution was used as a control and for the test, 1 mg/ml of a thermostable xylose isomerase was added to the solution. These solutions were incubated at 80° C. and each aliquot was removed at 0, 20, 60 and 180 min. after the beginning of the incubation. Each aliquot was analyzed with high performance liquid chromatography (column: UL-TRON PS80N (available from Shinwa Kako in Japan)), temperature: 50° C. flow rate: 0.9 ml/min., eluent: $H_2O$. The results are shown in FIG. 9.

Example 5 (pH dependence of coloring of fructose solution)

Figure 10:
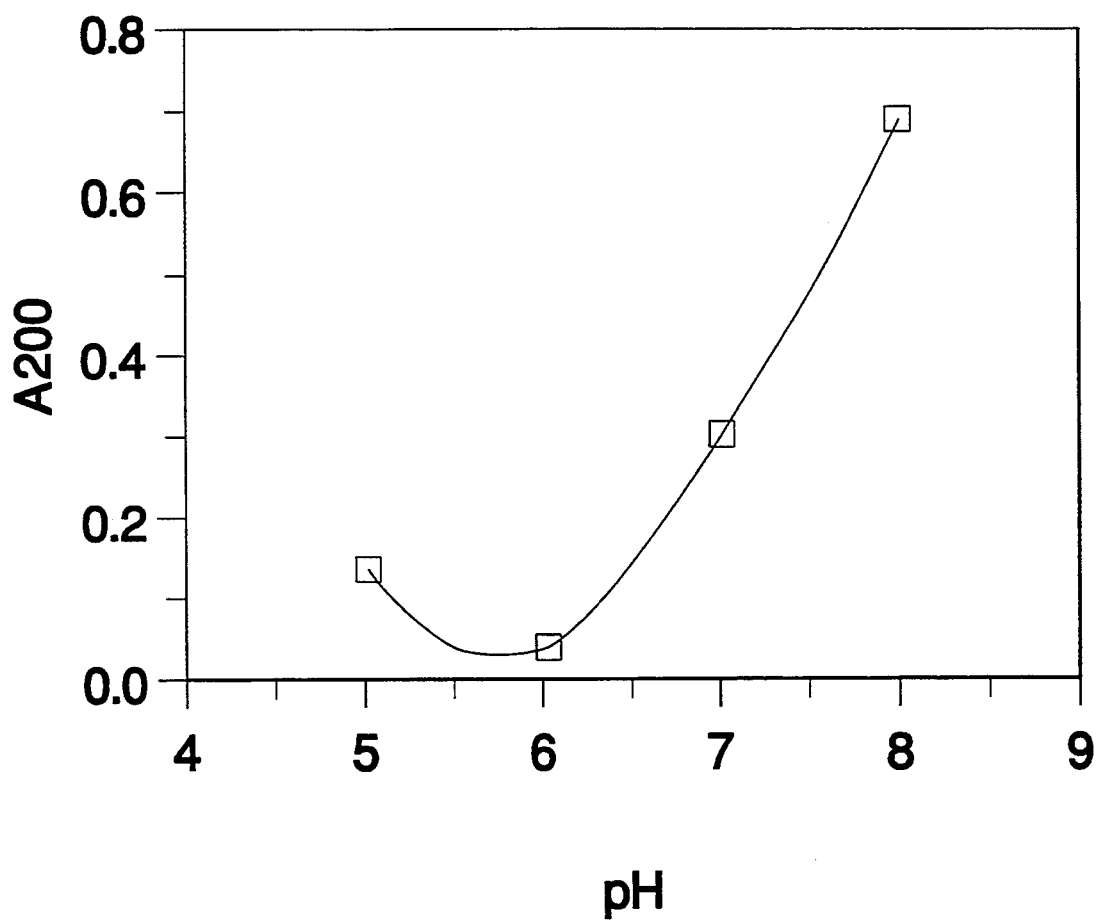
FIG. 10 illustrates a pH dependence of coloring of a fructose solution.

After incubation of the reaction mixture containing 25% (W/V) fructose, 25% (w/V) glucose and 100 mM triethanolamine buffer (pH 5, 6, 7 and 8) at 80° C. for 3h, coloring of each reaction mixture was assayed by measuring UV absorbance at 200 nm (A200) using a spectrophotometer. The results are shown in FIG. 10. As shown in FIG. 10, it is found that coloring is low within the pH range between 5 and 7.

It is possible to produce a large quantity of new thermophilic and thermostable xylose isomerase by the use of the xylose isomerase gene of *T. aquaticus* of the present invention.

Further, this xylose isomerase, unlike the known native *T. aquaticus* xylose isomerase, can be thermostabilized with magnesium which is an approved metal as a food additive, and then it is practically useful in production of fructose used as a food sweetener. Additionally, the optimal temperature of the present xylose isomerase is approximately at 95° C. which is higher than that of the known native *T. aquaticus* xylose isomerase and it is favorable for the production of fructose.

Also, according to the present method using the present thermostable xylose isomerase, it is possible to produce high concentrated fructose solution having very little color.

---

What we claim is:

1. An isolated gene from *Thermus aquaticus* consisting of the nucleotide sequence set forth in SEQ ID NO: 1 or consisting of a DNA sequence encoding the xylose isomerase having the amino acid sequence set forth in SEQ ID NO:2.

2. An expression vector comprising the isolated gene as claimed in claim 1 operably linked in proper reading frame to a promoter.

3. The expression vector of claim 2 wherein the promoter is the tac promoter, the cell wall protein (CWP) promoter, the phosphoglycerate kinase gene promoter, the alcohol dehydrogenase gene promoter, the glyceraldehyde phosphate dehydrogenase promoter, the glycerol kinase P1 gene promoter, the erythromycin resistance gene EP1 promoter or the phage T7 promoter.

4. A microorganism transformed with the expression vector of claim 2.

5. The transformed microorganism of claim 4, wherein the microorganism is selected from the group consisting of *Escherichia coli, Bacillus brevis, Saccharomyces cerevisiae, Streptomyces lividans* and *Bacillus subtilis*.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1805 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 288..1448

( x i ) SEQUENCE DESCRIPTION: SEQ ID NO:1:

```
GAGCTCCTCA  AGGAGATGTC  CGAAAGACTC  GCTCATCTCT  GCGCCATCGC  CCTGAGCACC          60

TTGGACCCTG  GGCTGGTGGT  CCTCGGCGGC  CCCCTCCGCC  GAGGCTGCCG  GGGAGAAGCT         120

TCTAGAGGAG  GTGCGGAAGC  CGGGCCTTTC  CCCGCTACGC  CCTGAAGGTG  CATGAGCCCG         180

ACCAGGTGGT  CCTTTCCCCC  TTTGGACGGG  ATGCGGCCCT  TCTGGGGGCA  GGCGCCTTGG         240

CCGCAAGCCG  ATTTGTGGAT  TCCCTGGCTT  TTGAGGAGGT  GATGTAG     GTG TAC GAG        296
                                                           Val Tyr Glu
                                                             1

CCC AAA CCG GAG CAC AGG TTT ACC TTT GGC CTT TGG ACT GTG GGC AAT               344
Pro Lys Pro Glu His Arg Phe Thr Phe Gly Leu Trp Thr Val Gly Asn
      5                  10                  15

GTG GGC CGT GAT CCC TTC GGG GAC GCG GTT CGG GAG AGG CTG GAC CCG               392
Val Gly Arg Asp Pro Phe Gly Asp Ala Val Arg Glu Arg Leu Asp Pro
 20                  25                  30                  35

GTT TAC GTG GTT CAT AAG CTG GCG GAG CTT GGG GCC TAC GGG GTA AAC               440
Val Tyr Val Val His Lys Leu Ala Glu Leu Gly Ala Tyr Gly Val Asn
```

-continued

|  | 40 | | | | | 45 | | | | | 50 | | | | |  |
|---|---|---|---|---|---|---|---|---|---|---|---|---|---|---|---|---|
| CTT | CAC | GAC | GAG | GAC | CTG | ATC | CCG | CGG | GGC | ACG | CCT | CCT | CAG | GAG | CGG | 488 |
| Leu | His | Asp | Glu | Asp | Leu | Ile | Pro | Arg | Gly | Thr | Pro | Pro | Gln | Glu | Arg | |
| | | | | 55 | | | | | 60 | | | | | 65 | | |
| GAC | CAG | ATC | GTG | AGG | CGC | TTC | AAG | AAG | GCT | CTC | GAT | GAA | ACC | GGC | CTC | 536 |
| Asp | Gln | Ile | Val | Arg | Arg | Phe | Lys | Lys | Ala | Leu | Asp | Glu | Thr | Gly | Leu | |
| | | | 70 | | | | | 75 | | | | | 80 | | | |
| AAG | GTC | CCC | ATG | GTC | ACC | GCC | AAC | CTC | TTC | TCC | GAC | CCT | GCT | TTC | AAG | 584 |
| Lys | Val | Pro | Met | Val | Thr | Ala | Asn | Leu | Phe | Ser | Asp | Pro | Ala | Phe | Lys | |
| | 85 | | | | | 90 | | | | | 95 | | | | | |
| GAC | GGG | GCC | TTC | ACG | AGC | CCG | GAC | CCT | TGG | GTT | CGG | GCC | TAT | GCC | TTG | 632 |
| Asp | Gly | Ala | Phe | Thr | Ser | Pro | Asp | Pro | Trp | Val | Arg | Ala | Tyr | Ala | Leu | |
| 100 | | | | | 105 | | | | | 110 | | | | | 115 | |
| CGG | AAG | AGC | CTG | GAG | ACC | ATG | GAC | CTG | GGG | GCA | GAG | CTT | GGG | GCC | GAG | 680 |
| Arg | Lys | Ser | Leu | Glu | Thr | Met | Asp | Leu | Gly | Ala | Glu | Leu | Gly | Ala | Glu | |
| | | | | 120 | | | | | 125 | | | | | 130 | | |
| ATC | TAC | GTG | GTC | TGG | CCG | GGC | CGG | GAG | GGA | GCT | GAG | GTG | GAG | GCC | ACG | 728 |
| Ile | Tyr | Val | Val | Trp | Pro | Gly | Arg | Glu | Gly | Ala | Glu | Val | Glu | Ala | Thr | |
| | | | 135 | | | | | 140 | | | | | 145 | | | |
| GGC | AAG | GCC | CGG | AAG | GTC | TGG | GAC | TGG | GTG | CGG | GAG | GCG | CTG | AAC | TTC | 776 |
| Gly | Lys | Ala | Arg | Lys | Val | Trp | Asp | Trp | Val | Arg | Glu | Ala | Leu | Asn | Phe | |
| | | 150 | | | | | 155 | | | | | 160 | | | | |
| ATG | GCC | GCC | TAC | GCC | GAG | GAC | CAG | GGA | TAC | GGG | TAC | CGG | TTT | GCC | CTC | 824 |
| Met | Ala | Ala | Tyr | Ala | Glu | Asp | Gln | Gly | Tyr | Gly | Tyr | Arg | Phe | Ala | Leu | |
| | 165 | | | | | 170 | | | | | 175 | | | | | |
| GAG | CCC | AAG | CCT | AAC | GAG | CCC | CGG | GGG | GAC | ATT | TAC | TTC | GCC | ACC | GTG | 872 |
| Glu | Pro | Lys | Pro | Asn | Glu | Pro | Arg | Gly | Asp | Ile | Tyr | Phe | Ala | Thr | Val | |
| 180 | | | | | 185 | | | | | 190 | | | | | 195 | |
| GGG | AGC | ATG | CTC | GCC | TTT | ATT | CAT | ACC | CTG | GAC | CGG | CCC | GAG | CGC | TTC | 920 |
| Gly | Ser | Met | Leu | Ala | Phe | Ile | His | Thr | Leu | Asp | Arg | Pro | Glu | Arg | Phe | |
| | | | | 200 | | | | | 205 | | | | | 210 | | |
| GGC | CTG | AAC | CCC | GAG | TTC | GCC | CAC | GAG | ACC | ATG | GCC | GGG | CTT | AAC | TTT | 968 |
| Gly | Leu | Asn | Pro | Glu | Phe | Ala | His | Glu | Thr | Met | Ala | Gly | Leu | Asn | Phe | |
| | | | 215 | | | | | 220 | | | | | 225 | | | |
| GTC | CAC | GCC | GTG | GCC | CAG | GCT | CTC | GAC | GCC | GGG | AAG | CTT | TTC | CAC | ATT | 1016 |
| Val | His | Ala | Val | Ala | Gln | Ala | Leu | Asp | Ala | Gly | Lys | Leu | Phe | His | Ile | |
| | | 230 | | | | | 235 | | | | | 240 | | | | |
| GAC | CTC | AAC | GAC | CAA | CGG | ATG | AGC | CGG | TTT | GAC | CAG | GAC | CTC | CGC | TTC | 1064 |
| Asp | Leu | Asn | Asp | Gln | Arg | Met | Ser | Arg | Phe | Asp | Gln | Asp | Leu | Arg | Phe | |
| | 245 | | | | | 250 | | | | | 255 | | | | | |
| GGC | TCG | GAG | AAC | CTC | AAG | GCG | GCC | TTT | TTC | CTG | GTG | GAC | CTC | CTG | GAA | 1112 |
| Gly | Ser | Glu | Asn | Leu | Lys | Ala | Ala | Phe | Phe | Leu | Val | Asp | Leu | Leu | Glu | |
| 260 | | | | | 265 | | | | | 270 | | | | | 275 | |
| AGC | TCC | GGC | TAC | CAG | GGC | CCC | CGC | CAC | TTT | GAC | GCC | CAC | GCC | CTG | CGT | 1160 |
| Ser | Ser | Gly | Tyr | Gln | Gly | Pro | Arg | His | Phe | Asp | Ala | His | Ala | Leu | Arg | |
| | | | | 280 | | | | | 285 | | | | | 290 | | |
| ACC | GAG | GAC | GAA | GAA | GGG | GTT | TGG | GCC | TTC | GCC | CGA | GGC | TGC | ATG | CGT | 1208 |
| Thr | Glu | Asp | Glu | Glu | Gly | Val | Trp | Ala | Phe | Ala | Arg | Gly | Cys | Met | Arg | |
| | | | 295 | | | | | 300 | | | | | 305 | | | |
| ACC | TAC | CTG | ATC | TTA | AAG | GAA | AGG | GCT | GAA | GCC | TTC | CGC | GAG | GAT | CCC | 1256 |
| Thr | Tyr | Leu | Ile | Leu | Lys | Glu | Arg | Ala | Glu | Ala | Phe | Arg | Glu | Asp | Pro | |
| | | 310 | | | | | 315 | | | | | 320 | | | | |
| GAG | GTC | AAG | GAG | CTT | CTT | GCC | GCT | TAC | TAT | CAA | GAA | GAT | CCT | GCG | GCC | 1304 |
| Glu | Val | Lys | Glu | Leu | Leu | Ala | Ala | Tyr | Tyr | Gln | Glu | Asp | Pro | Ala | Ala | |
| | 325 | | | | | 330 | | | | | 335 | | | | | |
| TTG | GCC | CTT | TTG | GGC | CCC | TAC | TCC | CGC | GAG | AAG | GCC | GAA | GCC | CTC | AAG | 1352 |
| Leu | Ala | Leu | Leu | Gly | Pro | Tyr | Ser | Arg | Glu | Lys | Ala | Glu | Ala | Leu | Lys | |
| 340 | | | | | 345 | | | | | 350 | | | | | 355 | |
| CGG | GCG | GAG | CTT | CCC | CTC | GAG | GCC | AAG | CGC | CGG | GGT | TAT | GCC | CTG | | 1400 |
| Arg | Ala | Glu | Leu | Pro | Leu | Glu | Ala | Lys | Arg | Arg | Gly | Tyr | Ala | Leu | | |
| | | | | 360 | | | | | 365 | | | | | 370 | | |

| | | | | | | | | | | | | | | | |
|---|---|---|---|---|---|---|---|---|---|---|---|---|---|---|---|
| GAA | CGC | CTG | GAC | CAG | CTG | GCG | GTG | GAG | TAC | CTC | CTG | GGG | GTG | CGG | GGG | 1448
| Glu | Arg | Leu | Asp | Gln | Leu | Ala | Val | Glu | Tyr | Leu | Leu | Gly | Val | Arg | Gly |
| | | 375 | | | | | 380 | | | | | 385 | | | |

```
TGAGGGCGGC CATCGGCTTG GACCTGGGAA CGAGCGGGCT CAAGGCCCTG GTGCTGGACG   1508
AGGAGGGGTA GAAAGCGCGC TGAGGCCCGG GCCCGGTACC CCCTTCACAC CCCGAGGCCG   1568
GGCTGGACGG AGCAGGACCC CCAGGACTGG GCCCGGGCCC TGAAGGAGGT GTTCCGGGCC   1628
CTGGCGCCGA AGCTTTCGGG CTTGGAGGTG GTGGGCCTGG GCTTTCCGG GCAGATGCAC    1688
GGGGCGGTCT TCCTGGACCG GGAGGGCCGT TTCCTCCTTC CTGCGCCCCT TTGGAACGAC   1748
CAGCGCACGG AGGAGGAAGT CCGGTGGATG GAAGAGGTCT TCCCTCGGCC CGAGCTC     1805
```

( 2 ) INFORMATION FOR SEQ ID NO:2:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Tyr Glu Pro Lys Pro Glu His Arg Phe Thr Phe Gly Leu Trp Thr
 1               5                  10                  15
Val Gly Asn Val Gly Arg Asp Pro Phe Gly Asp Ala Val Arg Glu Arg
                20                  25                  30
Leu Asp Pro Val Tyr Val Val His Lys Leu Ala Glu Leu Gly Ala Tyr
                35                  40                  45
Gly Val Asn Leu His Asp Glu Asp Leu Ile Pro Arg Gly Thr Pro Pro
        50                  55                  60
Gln Glu Arg Asp Gln Ile Val Arg Arg Phe Lys Lys Ala Leu Asp Glu
65                  70                  75                  80
Thr Gly Leu Lys Val Pro Met Val Thr Ala Asn Leu Phe Ser Asp Pro
                    85                  90                  95
Ala Phe Lys Asp Gly Ala Phe Thr Ser Pro Asp Pro Trp Val Arg Ala
                100                 105                 110
Tyr Ala Leu Arg Lys Ser Leu Glu Thr Met Asp Leu Gly Ala Glu Leu
            115                 120                 125
Gly Ala Glu Ile Tyr Val Val Trp Pro Gly Arg Glu Gly Ala Glu Val
        130                 135                 140
Glu Ala Thr Gly Lys Ala Arg Lys Val Trp Asp Trp Val Arg Glu Ala
145                 150                 155                 160
Leu Asn Phe Met Ala Ala Tyr Ala Glu Asp Gln Gly Tyr Gly Tyr Arg
                    165                 170                 175
Phe Ala Leu Glu Pro Lys Pro Asn Glu Pro Arg Gly Asp Ile Tyr Phe
                180                 185                 190
Ala Thr Val Gly Ser Met Leu Ala Phe Ile His Thr Leu Asp Arg Pro
            195                 200                 205
Glu Arg Phe Gly Leu Asn Pro Glu Phe Ala His Glu Thr Met Ala Gly
        210                 215                 220
Leu Asn Phe Val His Ala Val Ala Gln Ala Leu Asp Ala Gly Lys Leu
225                 230                 235                 240
Phe His Ile Asp Leu Asn Asp Gln Arg Met Ser Arg Phe Asp Gln Asp
                    245                 250                 255
Leu Arg Phe Gly Ser Glu Asn Leu Lys Ala Ala Phe Phe Leu Val Asp
                260                 265                 270
Leu Leu Glu Ser Ser Gly Tyr Gln Gly Pro Arg His Phe Asp Ala His
            275                 280                 285
```

-continued

| | | | | | | | | | | | | | | |
|---|---|---|---|---|---|---|---|---|---|---|---|---|---|---|
|Ala|Leu 290|Arg|Thr|Glu|Asp|Glu 295|Glu|Gly|Val|Trp|Ala 300|Phe|Ala|Arg|Gly|
|Cys 305|Met|Arg|Thr|Tyr|Leu 310|Ile|Leu|Lys|Glu|Arg 315|Ala|Glu|Ala|Phe|Arg 320|
|Glu|Asp|Pro|Glu|Val 325|Lys|Glu|Leu|Leu|Ala 330|Ala|Tyr|Tyr|Gln|Glu 335|Asp|
|Pro|Ala|Ala|Leu 340|Ala|Leu|Leu|Gly|Pro 345|Tyr|Ser|Arg|Glu|Lys 350|Ala|Glu|
|Ala|Leu|Lys 355|Arg|Ala|Glu|Leu|Pro 360|Leu|Glu|Ala|Lys|Arg 365|Arg|Arg|Gly|
|Tyr|Ala 370|Leu|Glu|Arg|Leu|Asp 375|Gln|Leu|Ala|Val|Glu 380|Tyr|Leu|Leu|Gly|
|Val 385|Arg|Gly| | | | | | | | | | | | | |